(12) United States Patent
Spurr et al.

(10) Patent No.: US 6,381,418 B1
(45) Date of Patent: Apr. 30, 2002

(54) PRINT HAVING INFORMATION ASSOCIATED WITH THE PRINT STORED IN A MEMORY COUPLED TO THE PRINT

(75) Inventors: Robert W. Spurr; Babak Tehranchi; Kurt M. Sanger, all of Rochester; Timothy J. Tredwell, Fairport, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/372,329

(22) Filed: Aug. 11, 1999

(51) Int. Cl.$^7$ .................. G03B 13/04; G03B 27/52; G03B 29/00; A47G 1/06
(52) U.S. Cl. .................. 396/310; 355/40; 40/701; 40/711; 396/429
(58) Field of Search .................. 396/310, 312, 396/321, 429, 56; 360/1, 2; 40/455, 457, 124.04, 124.06, 700, 701, 711, 717; 434/311; 355/40, 42

(56) References Cited

U.S. PATENT DOCUMENTS

| | | | |
|---|---|---|---|
| 4,270,854 A | 6/1981 | Stemme et al. | 396/312 |
| 4,600,280 A | 7/1986 | Clark | 352/37 |
| 4,806,958 A | 2/1989 | Momot et al. | 396/208 |
| 4,905,029 A | 2/1990 | Kelley | 396/312 |
| 4,990,092 A | 2/1991 | Cummings | 434/317 |
| 5,290,190 A | 3/1994 | McClanahan | 434/317 |
| 5,521,663 A | 5/1996 | Norris, III | 396/312 |
| 5,528,222 A | 6/1996 | Moskowitz et al. | 340/572.7 |
| 5,574,519 A | 11/1996 | Manico et al. | 396/429 |
| 5,584,070 A * | 12/1996 | Harris et al. | 396/429 |
| 5,721,992 A * | 2/1998 | Chovanes | 396/312 |
| 5,768,633 A * | 6/1998 | Allen et al. | 396/310 |
| 5,774,752 A | 6/1998 | Patton et al. | 396/312 |
| 5,913,088 A * | 6/1999 | Moghadam et al. | 396/319 |
| 6,075,950 A * | 6/2000 | Stephenson | 396/312 |
| 6,173,119 B1 * | 1/2001 | Manico et al. | 396/310 |
| 6,263,310 B1 * | 7/2001 | Loudermilk et al. | 40/717 |
| 6,282,819 B1 * | 9/2001 | Gu | 40/717 |

\* cited by examiner

*Primary Examiner*—Christopher E. Mahoney
(74) *Attorney, Agent, or Firm*—Walter S. Stevens

(57) ABSTRACT

A print having information associated with the print stored in a memory coupled to the print. A print, processed by an image processing apparatus, having an attached memory for storing detailed information about the print and allowing contactless access using an electromagnetic frequency signal. A transceiver, connected to a control logic device, communicates with a transponder that is attached to the print substrate and is integrally coupled to the memory. The transponder is capable of receiving a first electromagnetic field (frequency) from the transceiver and deriving power and address information from the first frequency, then generates a second electromagnetic field (frequency) in response, where the second electromagnetic field is characteristic of the data stored in memory.

40 Claims, 4 Drawing Sheets

PRINT HAVING INFORMATION ASSOCIATED WITH THE PRINT STORED IN A MEMORY COUPLED TO THE PRINT

FIELD OF THE INVENTION

This invention generally relates to prints processed by image processing apparatus and more particularly relates to a print having information associated with the print stored in a memory coupled to the print.

BACKGROUND OF THE INVENTION

There can be a considerable amount of information associated with an image produced on a print by an image processing device. It is beneficial to have this information integrally attached to the print and, therefore, readily available for access. This is particularly true for high-quality image prints such as those produced by a digital proofing system, such as the "APPROVAL Digital Proofing System"™ available from the Eastman Kodak Company, located in Rochester, N.Y. For such a system, an image on an output print is carefully analyzed for its overall appearance and color content. Adjustments for improving appearance and color are made using the output print. In practice, the output print from such a system is also used as a contractual tool, requiring customer approval before an expensive four-color printing operation is initiated. For a print from such a digital proofing system, because such a system is designed to emulate printing press output, it is important to know the exact conditions under which an image was printed. Variables such as dot shape, screen angle, screen ruling, densities of component colors and dot gain adjustments can be modified for images printed from such systems, depending on corresponding characteristics of the target four-color printing system that will be used for the finished product. Because an image is prepared using any one of a number of digital prepress systems, it is also beneficial to identify the specific system upon which the image has been processed, along with information identifying a filename associated with the image that is reproduced.

To provide information on the proofing variables used to prepare a specific digital proof, and to provide other identifying information about the proof, proofing systems such as the "APPROVAL Digital Proofing System"™ record key identification and image processing variables on the proof itself, typically printed apart from the image, such as in an extreme corner of a proof sheet. This method serves the needs of an observer viewing the proof, but does not easily allow automated methods to facilitate access of this information for display, archiving, or the like.

The need to store detailed information about a printed image is also an important requirement for a diagnostic image, such as an image obtained by scanning using X-rays, ultrasound, or CAT (Computerized Axial Tomography). Such images typically have a significant amount of information related to them. For example, in the case of a medical diagnostic image, detailed information on patient name, patient age, patient history, physician's name, facility name, and other information accompany the image so that the image can be correctly analyzed and tracked. Methods used for attaching detailed information with such a diagnostic image include encoding information on the edge of the film substrate containing the image.

In addition, photographic negative film can be encoded with information to assist in film processing. For example, a negative film cassette using APS (Advanced Photo System) technology, such as the KODAK "ADVANTIX"™ film available from the Eastman Kodak Company allows a camera to record information on those conditions under which a negative film was exposed when taking a photograph. This information is recorded on a thin magnetic layer disposed on the negative film substrate. Using the APS technology, when a photoprocessing apparatus creates a print from the developed negative film, the apparatus then prints information obtained from the magnetic layer disposed onto the back of the print. Typically, date and time the print was taken are back-printed on the reverse side of the print. However, other than back-printing of this relatively small amount of data, other useful information is not encoded onto the print.

Thus, it is desirable to attach identifying and processing information to the print. In this regard, the need for attaching information to an output print is based on how a print is used. Factors that determine how useful it is to attach information to a print include the overall value of a print, the complexity and significance of setup conditions required for obtaining and printing an image on a print in a specific way, and the desirability of obtaining more detailed information about the subject of an image appearing on the print. From this perspective, the capability to integrally attach identifying and processing information to a print serves a wide range of image processing functions including, but not limited to, digital proofing, diagnostic imaging, professional and portrait imaging, and aerial photography.

Conventional methods for attaching information about a printed image on a print include providing information on an attached magnetic strip. This solution allows storage of some data, but has inherent disadvantages. For example, magnetically encoded media must be protected from magnets or strong electromagnetic fields. Reading information from this type of media requires placing the media, in proper orientation, into a reader device. Determining whether or not a specific image is included in a collection of prints stacked or stored together requires manually searching through the collection of prints or handling prints individually, so as to feed each print to the reader device.

Attachment of an electronic memory component to the print substrate has inherent disadvantages when physical connection must be made to the memory component for recording or obtaining information stored in the memory component. Connectors add cost and present reliability problems caused by dust and dirt and repeated connection/ disconnection duty cycles.

RFID (Radio Frequency Identification) tags having an integrally attached memory are commercially available and are used in applications where it is useful to store unique identifying information that is attached to an item. RFID tags have been proposed for use in applications with passports and credit cards, such as is disclosed in U.S. Pat. No. 5,528,222 to Moskowitz et al. A commercially available "TAG-IT INLAY"™, available from Texas Instruments, Incorporated, located in Dallas, Tex., USA, can be used to provide identifying information about a device to which it is attached. This relatively thin, flexible type of RFID tag can be used in an application that previously required a label or bar code. The applications noted in U.S. Pat. No. 5,528,222 and mentioned for the "TAG-IT INLAY"™ device and similar devices are primarily used for identification purposes, such as for employee badges, inventory control, and credit card account identification.

Attachment of a memory to a consumable used as the input "raw material" for an image processing apparatus is disclosed in commonly assigned copending application "A PRINTER AND METHOD THEREFOR ADAPTED TO SENSE DATA UNIQUELY ASSOCIATED WITH A CONSUMABLE LOADED INTO THE PRINTER" U.S. Ser. No. 09/334,375). This copending patent application discloses the use of an RFID transponder component having a memory integrally attached thereto, the memory being connected to a consumable item. With this feature, an image processing apparatus can identify each consumable type loaded therein and adapt its operation accordingly to provide an optimum image. However, this copending application discloses use of such a memory device for an input consumable only. However, as described hereinbelow, an output print produced from such a system would also benefit from attachment of a memory component.

Therefore, it can be seen that there is a need for attachment of a memory to a print output provided by an image processing apparatus.

SUMMARY OF THE INVENTION

It is an object of the present invention to provide, from an image processing apparatus, an output print having an attached memory that is capable of storing information associated with the image printed thereon.

According to an aspect of the present invention, a print output from an image processing apparatus comprises an attached non-volatile semiconductor memory component that is integrally coupled to a transponder. The memory component may be, for example, an EEPROM (Electically Erasable Programmable Read-Only Memory). Stored in the memory are encoded data indicative of the identity of the images on the print and indicative of specific conditions under which the print was processed. The transponder is capable of receiving a first electromagnetic field (frequency) generated by a radio-frequency transceiver unit. The transponder provides power to its coupled semiconductor circuitry as the transponder receives the first electromagnetic field or frequency. When the transponder circuitry is powered, the component generates a second electromagnetic field (frequency) in response to the first electromagnetic field. The second electromagnetic field is conditioned by information stored in the memory.

A feature of the present invention is the provision of a transceiver that stores information about a print and its images on a memory that is attached to a print substrate. A related feature of the present invention is the ability of a transceiver to retrieve stored information from this memory.

A further feature of the present invention is the provision of a transceiver that selectively addresses a specific transponder from among a plurality of transponders attached to respective ones of a collection prints and to transfer data to or from that transponder, where the data transferred is indicative of image identity or print processing.

An advantage of the present invention that use thereof allows detailed information uniquely associated with a print to be integrally attached to the print for automated reading and retrieval.

A further advantage of the present invention that use thereof allows automated identification of a print when that print is included in a collection of prints, each print in this collection having an attached memory. In this regard, the present invention allows an operator to quickly scan a box containing a plurality of prints and to quickly identify and independently access information concerning each print in the box, without handling the prints individually. This facilitates inventory control and archiving of processed prints.

Yet a further advantage of the present invention that use thereof allows storage, on the print itself, information concerning how the print was produced, including processing variables.

A further advantage of the present invention that use thereof provides a contactless communication interface, accessing data without requiring that electrical contact be made to corresponding contacts being mounted on a print.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIG. 3b is an enlarged plan view of a transponder integrated circuit attached to the antenna shown in FIG. 3a.

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

For the description that follows, the general term "print" is used herein to indicate an output image reproduced onto a substrate, where the image is reproduced using ink, dyes, or known exposure methods. By way of example only, and not by way of limitation, a print, generally numbered 30 in the following description, could be any of the following:

a printed output sheet, such as from a proofing system, including digital proofing systems that use thermal print technologies, from inkjet printers, or from photofinishing printers that use photosensitive film or paper that is exposed to a light source and developed using a subsequent chemical process for creating an image;

a photographic print;

a developed X-ray, ultrasound, or other diagnostic image; or an aerial photograph.

A substrate, generally numbered 42 in the following description, is typically in sheet form and may include, for example, film, paper, cardboard, textile, vinyl, or other material capable of accepting a printed image.

Figure 1:
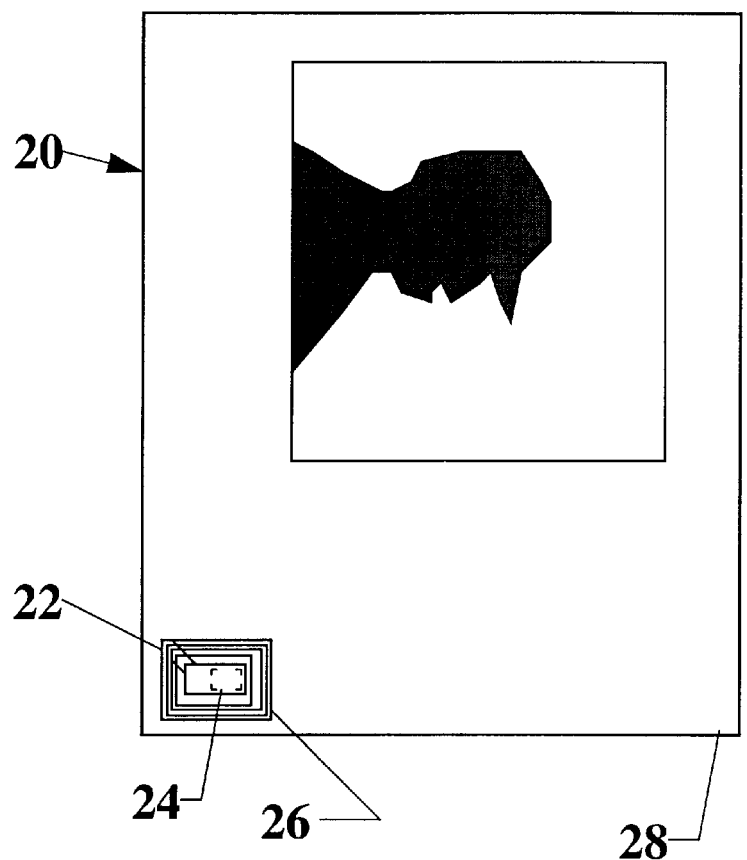
FIG. 1 is a plan view of a proof sheet output from a digital proofing system, the proof sheet having an attached transponder.

FIG. 1 shows a transponder 22, which may be a "TAG-IT INLAY"™, attached to a digital proof sheet 20 imaged onto a substrate 28, which may be paper. Transponder 22 includes a memory 24, an antenna 26, and RF communication and power supply circuitry. Transponder 22 can be attached to the front or back of digital proof sheet 20 using an adhesivetape backing or can other attachment arrangement, as described hereinbelow.

Referring again to FIG. 1, transponder 22 is shown attached along an edge of paper substrate 28, away from an image area of proof sheet 20. However, it may be appreciated that this is but one possible arrangement, because, using any of the attachment methods described hereinbelow, transponder 22 may be attached in any suitable position on proof sheet 20.

It is useful to note that similar methods of attachment to the substrate as described for digital proof sheet 20 in FIG. 1 and as described hereinbelow may alternately be used for any type of print 30, such as a photographic print, X-ray or other diagnostic image, aerial photograph, or other printed output.

Figure 2:
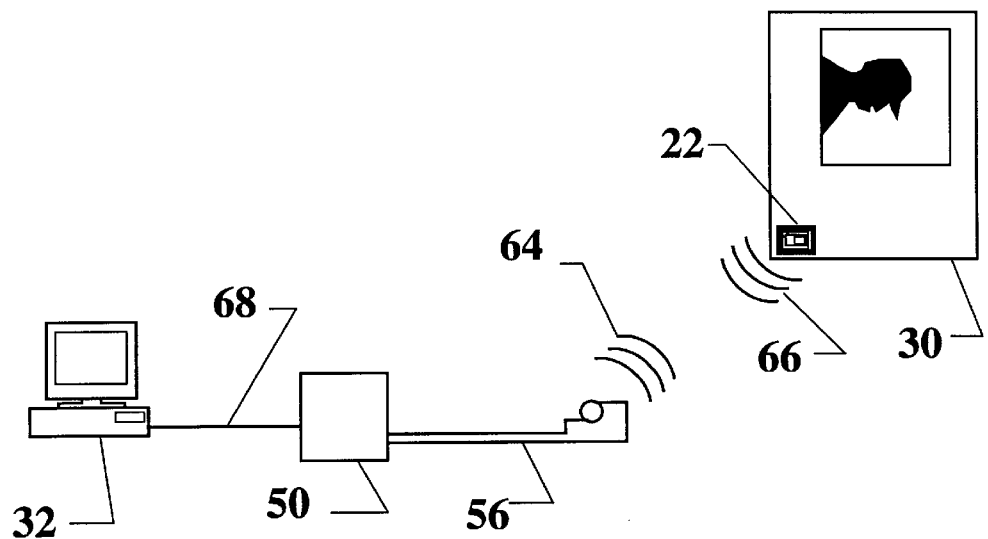
FIG. 2 is a schematic representation showing communication between a transponder and a transceiver, the transponder being attached to a print.

FIG. 2 shows, in schematic form, a system for programming or retrieving information from print 30 which has transponder 22 attached thereto. Print 30 itself may be the previously mentioned proof sheet 20 or a photographic print, or any other type of print. In this arrangement, a transceiver 50 is connected to a computer 32. Such a transceiver 50 may be, for example, a "HOUSED READER AND ANTENNA" transceiver, part number RI-K01-320A-00, available from Texas Instruments, Incorporated, located in Dallas, TEX. USA.

Transceiver 50 connects to an antenna 56. In operation, transceiver 50 is capable of transmitting a first electromagnetic field (frequency) 64 of a first predetermined frequency, for reasons disclosed presently. Transceiver 50 is also capable of receiving a second electromagnetic field (frequency) 66 of a second predetermined frequency, for reasons disclosed presently. Typically, but not necessarily, the same frequency serves for both first and second electromagnetic fields 64 and 66.

Transponder 22, itself, is a relatively low-power device that derives its source power from the first electromagnetic field 64 emitted by transceiver 50. In this regard, communication via antenna 56 between transceiver 50 and transponders 22 can take place over a limited distance.

Referring again to FIG. 2, transceiver 50 is electrically coupled to computer 32, such as by means of a signal interface 68, which signal interface 68 may be, for example, a standard RS-232C serial connection. This connection allows computer 32 to control the operation of transceiver 50 so that transceiver 50 can successively poll one or more transponders 22 in order to access information about one or more prints 30. Computer 32, which may be a standard personal computer, can be programmed to read data from the print (as accessed by transceiver 50) and then to display or to process this data, or to write data to the print, using techniques well known in the programming art.

It is important to note that computer 32 may alternately be embodied within transceiver 50, such as in a "hand-held" reader device. Using this alternate arrangement, an operator can encode information onto print 30 or decode information from print 30 without requiring connection to separate computer 32. This arrangement would be advantageous, for example, for data gathering or image identification purposes.

Figure 4:
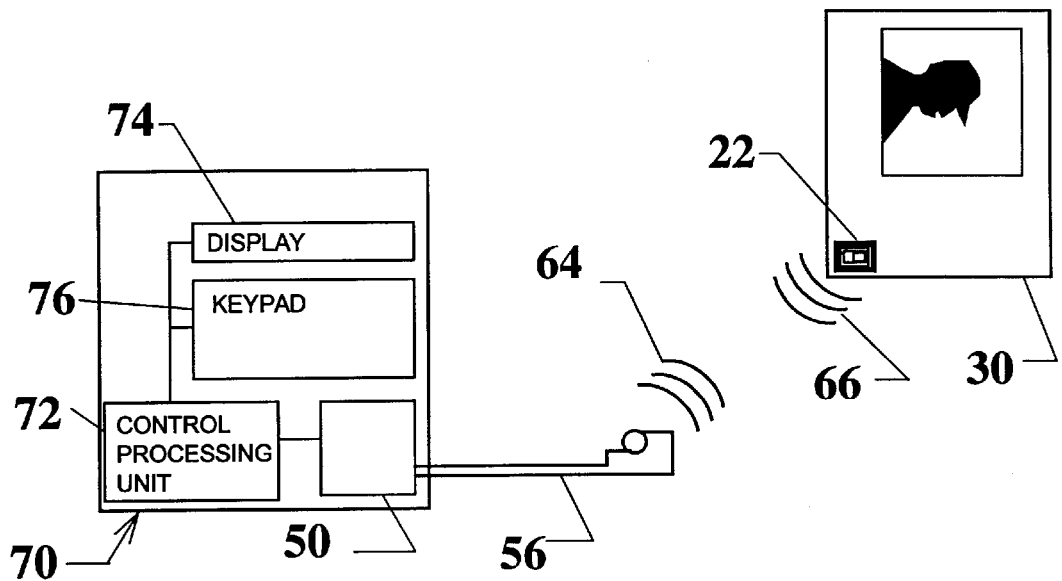
FIG. 4 is a schematic representation showing use of a hand-held reader device.

FIG. 4 schematically shows an alternate hand-held reader 70. For this configuration of the invention, a control processing unit 72 performs logic control functions necessary to operate transceiver 50, which communicates with transponder 22 on print 30 in the same manner as described above with reference to FIG. 2. A display 74, such as an LCD (Liquid-Crystal Display) well-known in the electronics instrumentation art, displays information read from transponder 22. A keypad 76 allows entry of data for writing information to transponder 22.

Transceiver 50 Communication With Transponder 22

Referring to FIGS. 1 and 4, it is instructive to note how transceiver 50 communicates with transponder 22. Transponder 22 is tuned to a carrier frequency emitted by transceiver 50. By way of example only, but not by way of limitation, this carrier frequency signal is in the RF (Radio Frequency) electromagnetic spectrum. In this manner, the invention uses a transceiver 50 and transponder 22 tuned to an RF frequency. However, the carrier frequency signal need not be in the RF range; rather, the carrier frequency may be at a microwave frequency.

Upon receiving an initial signal from transceiver 50, transponder 22 circuitry obtains, from the emitted electromagnetic energy, sufficient energy to provide source voltage for its internal circuitry. Thus, no battery is needed to separately power transponder 22.

When a plurality of transponders are used, each transponder 22 is individually programmed with an unique identifying address code (ID). As a final stage in manufacture, each transponder 22 is programmed to store its ID along with other data that is characteristic of the images, composition, and processing of print 30 to which transponder 22 is attached. Each transponder 22 is manually attached to print 30 as a final assembly stage. Other attachment methods are possible, as is described presently. Transceiver 50 has both read and write access to memory data stored by transponder 22.

To communicate with transponder 22, transceiver 50 encodes a unique identifying address code as part of its emitted signal, along with a command to read data from or to write data to ("program") transponder 22. Transponder 22 responds to transceiver 50 communication when it has been addressed correctly.

Methods of Attachment for Transponder 22

As noted hereinabove, transponder 22, which may be a "TAG-IT INLAY"™, is provided on adhesive-backed material for attachment to the print substrate. However, other methods of attachment are possible for transponder 22 within the scope of the present invention.

For example, as one method of attachment, transponder 22 can be laminated onto print 30. That is, digital proof sheet 20 will undergo a lamination process during final preparation. Alternately, transponder 22 can be embedded within print 30 as a during manufacture of print 30 or during preparation of print 30 for imaging. In this regard, transponder 22 may be embedded within paper substrate 28 of digital proof sheet 20 or within the film substrate used for an X-ray or other diagnostic image.

Figure 3A:
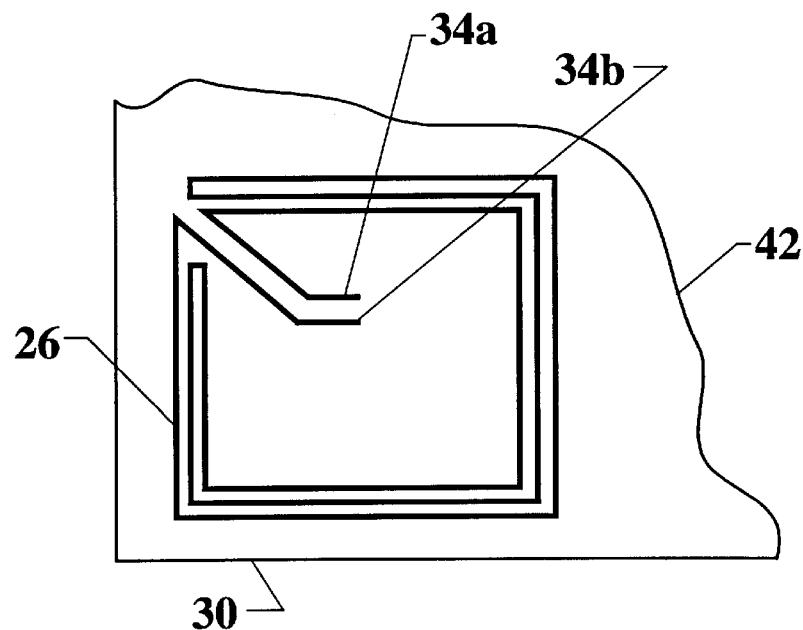
FIG. 3a is an enlarged plan view of an antenna provided on an edge of a print.
Figure 3B:
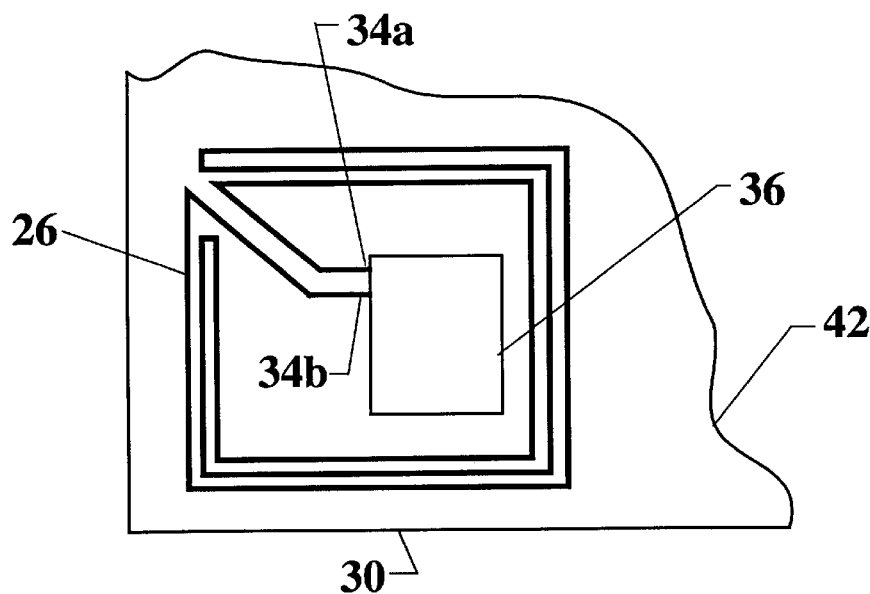

Antenna 26 is integrally formed with transponder 22 in the standard "TAG-IT INLAY"™ configuration. However, antenna 26 could be separately provided on a substrate material 42 as shown in FIGS. 3a and 3b. This arrangement of the invention would then allow a transponder integrated circuit 36 to be handled separately and affixed to substrate material 42 after programming, as shown in FIG. 3b. FIG. 3a shows a trace pattern of antenna 26 printed directly onto substrate material 42. A pair of antenna contacts 34a and 34b are accessible for connection to transponder integrated circuit 36. FIG. 3b shows transponder IC 36 connected to antenna contacts 34a and 34b. Alternately, antenna 26 could be embedded within substrate material 42, with contacts 34a and 34b extended to the surface of substrate material 42 for connection with transponder integrated circuit 36.

Programming the Memory and Memory Contents

Transponder 22 that is attached to print 30 can be programmed so that it reads at any time before, during, and after print 30 is processed to contain images. In this regard, transponder 22 is programmed with identifying and process variable information for digital proof sheet 20 after the image is applied onto substrate paper 28. In the case of the KODAK "APPROVAL Digital Proofing System"™, this process involves transfer of the four-color image from an intermediate receiver sheet onto paper substrate 28, using a thermal lamination transfer sequence. Computer 32 programs transponder 22 with identifying and process information based on variables used in the preparation of images intended for reproduction onto digital proof sheet 20.

By way of example only and not by way of limitation, the data stored in memory 24 of transponder 22 that is attached to paper substrate 28 may be any of the exemplary data displayed in Table 1 hereinbelow.

TABLE 1

Data Stored in Transponder 22 for Digital Proof Sheet 20

| Data Stored | Number of Bits | Description |
| --- | --- | --- |
| Proofing System Identifier | 8 | An 8-bit number encoding the type of digital proofing system that printed the image. |
| Filename | 128 | ASCII-encoded filename of source file(s) for image(s) on digital proof sheet 20. |
| Date/time stamp | 64 | Encoded data containing date and time identification for digital proof sheet 20. |
| Dot gain | 256 | Encoded values of dot gain for different dot percentages, as applied by the proofing system. |
| Density settings | 128 | Encoded density settings for component colors printed on digital proof sheet 20. (Typically, process colors cyan, magenta, yellow, and black are used.) |
| Dot shape | 32 | Encoded value indicating shape of halftone dots used on digital proof sheet 20 images. |
| Screen ruling | 16 | Encoded value giving screen ruling for halftone dots. |
| Screen angles | 32 | Encoded values of screen angles for component colors printed on digital proof sheet 20. |
| Paper type | 16 | Encoded value giving intended paper type for digital proof sheet 20. |
| Thermal donor batch ID | 64 | Encoded batch identifying information for thermal donor used to create digital proof sheet 20. |

As Table 1 shows, memory 24 includes information on numerous processing variables, including data on the consumable color donor materials used to print the image. Availability of this data facilitates assessment of digital proof sheet 20 and, for example, allows a program running on computer 32 to access and display a significant amount of information concerning digital proof sheet 20.

By way of example only and not by way of limitation, the data stored in memory 24 of transponder 22, that is attached to print 30 when print 30 uses an X-ray film substrate, may be any of the exemplary data displayed in Table 2 hereinbelow.

TABLE 2

Data Stored in Transponder 22 for Print 30 on X-ray Film Substrate

| Data Stored | Number of Bits | Description |
| --- | --- | --- |
| X-ray System Identifier | 8 | An 8-bit number encoding the type of diagnostic system that exposed the image. |
| Filename | 128 | ASCII-encoded filename of a digital file storing the image data. |
| Date/time stamp | 64 | Encoded data containing date and time identification for the X-ray. |
| Patient ID | 256 | Name and account number of subject patient. |
| Medical history | 256 | Encoded data including highlights of patient medical history, including age, known conditions, medications, surgery performed. |
| Doctor ID | 256 | Name and account number of physician. |

A feature of transponder 22 is its ability to temporarily disable a device or to lock individual memory pages in memory. This feature prevents erasure and loss of important data concerning the printed image. At the same time, because write operation for individual memory pages can be enabled, updated information can be provided about the subject of the printed image after transponder 22 is initially programmed by computer 32.

Communication With Multiple Prints

Computer 32 can be used to poll a collection of multiple prints 30, each having an attached transponder 22, and to locate and communicate with a specific print 30 in the collection. This capability facilitates archiving, where multiple prints 30 might be included in a folder. This same capability would, for example, automate scanning of a collection of prints 30, such as where multiple prints 30 are collected in a folder, to determine if a desired print 30 is in that folder.

There are a number of possible polling techniques that allow transceiver 50 to selectively communicate with a plurality of transponders 22, one at a time. Unique ID information can be assigned to each transponder 22, so that first electromagnetic field 64 emitted from transceiver 50 includes the coded ID information.

Another alternative polling technique employs a "non-collision" algorithm for communicating with multiple transponders grouped in a confined area. According to one embodiment of this algorithm, the algorithm uses a loop that proceeds in steps to increase transceiver 50 output power from an initial relatively low value as transceiver 50 repeatedly polls for a transponder 22. As soon as it detects a transponder 22, transceiver 50 communicates with the transponder 22, then temporarily disables the transponder 22. Transceiver 50 then sequentially repeats polling in this fashion, incrementing its output power level with each polling operation, to locate, communicate with, and then temporarily disable the next available transponder 22. In this way, transceiver 50 communicates with multiple transponders 22 in order of their return signal strength, until each transponder 22 has been contacted.

While the invention has been described with particular reference to its preferred embodiments, it will be understood by those skilled in the art that various changes may be made and equivalents may be substituted for elements in the preferred embodiments without departing from the scope of the invention. For example, computer 32 could be incorporated in the image processing apparatus itself. With this arrangement, the image processing apparatus that produces print 30 automatically prepares and programs transponder 22 for attachment to the print 30 substrate. Transponder 22 could be automatically attached to print 20 or could be provided for attachment by an operator as part of a post-printing or finishing process. As another example, transponder 22 could be built into the substrate sheet itself and could thereby be "invisible" to an operator or user of the print.

There are a number of possible alternate arrangements for integrating antenna 26 onto or within the print substrate. For example, antenna 26 could be imprinted onto a surface of the substrate by the image processing apparatus. As another example, antenna 26 could be integrated into the substrate material, as part of manufacture or processing, with contacts 34a/b provided for attachment of transponder integrated circuit 36.

Within the scope of the present invention are any number of possible arrangements of memory contents, as indicated in the exemplary description for Tables 1 and 2 hereinabove. Any one of known digital data encoding methods could be used to compress stored data in memory. Where it is advantageous to store more information than can be contained on a single transponder, multiple transponders could be affixed to the substrate.

Therefore, what is provided is a print having information associated with the print stored in a memory coupled to the print.

PARTS LIST

20. Proof sheet
22. Transponder
24. Memory
26. Antenna
28. Paper substrate
30. Print
32. Computer
34a, 34b. Antenna contacts
36. Transponder IC
42. Substrate material
50. Transceiver
56. Antenna
64. First electromagnetic field
66. Second electromagnetic field
68. Signal interface

What is claimed is:

1. A storage apparatus for storing data on an output print produced by an image processing apparatus, comprising:
    (a) a memory coupled to the output print, said memory adapted to store computer-readable data associated with an image;
    (b) a transponder integrally coupled to said memory, said transponder adapted to receive a first electromagnetic field and, in response to the first electromagnetic field received thereby, generating a second electromagnetic field, the second electromagnetic field being characteristic of the data stored in said memory;
    (c) a transceiver spaced-apart from the output print for transmitting the first electromagnetic field and for sensing the second electromagnetic field; and
    (d) a logic processor coupled to said transceiver, said logic processor adapted to communicate with said transceiver for facilitating exchange of data between said transceiver and said memory.

2. The storage apparatus of claim 1, wherein said transceiver transmits the first electromagnetic field at a predetermined first frequency.

3. The storage apparatus of claim 1, wherein said transceiver receives the second electromagnetic field at a predetermined second frequency.

4. The storage apparatus of claim 1, wherein said memory is adapted to store image processing data associated with the image.

5. The storage apparatus of claim 1, wherein said logic processor is a computer.

6. The storage apparatus of claim 1, further comprising:
    (a) a plurality of said memories coupled to respective ones of a plurality of the output prints; and
    (b) a plurality of said transponders coupled to respective ones of said memories.

7. Storage apparatus of claim 1 and wherein power for powering the transponder is derived solely from the first electromagnetic field, and wherein the memory and transponder are mounted on or embedded within a substrate upon which the print is printed, and wherein the first electromagnetic field and second electromagnetic field travel through the air.

8. A print, comprising:
    (a) a substrate;
    (b) a memory coupled to said substrate, said memory adapted to store data therein;
    (c) a transponder connected to said substrate and integrally coupled to said memory, said transponder adapted to receive a first electromagnetic field and, in response to the first electromagnetic field received thereby, generate a second electromagnetic field, the second electromagnetic field being characteristic of the data stored in said memory.

9. The print of claim 8, wherein said substrate material comprises an antenna coupled to said transponder.

10. The print of claim 8, wherein said memory has image processing data stored therein.

11. The print of claim 8, wherein said memory is a read/write memory.

12. The print of claim 8, wherein said substrate is paper.

13. The print of claim 8, wherein said substrate is film.

14. The print of claim 8 and wherein the print is a digital proof.

15. The print of claim 14 and wherein the transponder includes an antenna for receiving the first electromagnetic field to provide the sole power for the transponder and memory.

16. The print of claim 15 and wherein the memory stores a file identifier for the print.

17. The print of claim 16 and wherein the memory stores information in compressed form.

18. The print of claim 15 and wherein the memory is embedded within a substrate upon which the print is printed.

19. The print of claim 15 and wherein the antenna is printed on the substrate.

20. The print of claim 8 and wherein the print is an x-ray or other diagnostic image.

21. The print of claim 20 and wherein the transponder includes an antenna for receiving the first electromagnetic field to provide the sole power for the transponder and memory.

22. The print of claim 21 and wherein the memory stores a file identifier for the print.

23. The print of claim 21 and wherein the memory stores information in compressed form.

24. The print of claim 21 and wherein the memory is embedded within a substrate upon which the print is printed.

25. The print of claim 21 and wherein the antenna is printed on the substrate.

26. A method for determining the presence of a particular print in a folder including a plurality of prints, the system comprising:

providing a folder having a plurality of prints including the particular print, the particular print including a memory supported on or within a substrate of the particular print, the memory storing data and the particular print including a transponder integrally coupled to the memory and supported on or within the substrate of the particular print;

operating the transponder to receive though the air a first electromagnetic field and, in response to the first electromagnetic field received thereby, generating a second electromagnetic field, the second electromagnetic field being characteristic of the data stored in the memory;

operating a transceiver spaced apart from the print to transmit the first electromagnetic field through the air and for sensing the second electromagnetic field, the first electromagnetic field providing the sole source of power for the transponder; and communicating information representing data stored in the memory to a logic processor coupled to the transceiver for determining the presence of the particular print.

27. The method of claim 26 and wherein each of the prints in the folder includes a respective memory supported on or within a substrate of the respective print, the respective memory storing respective data relative to the identity of the respective print, and the respective print including a transponder integrally coupled to the memory and supported on or within the substrate of the respective print, and wherein the respective prints are polled to determine presence of the prints within the folder.

28. A method of communicating with a print, the method comprising:

providing a print including a memory supported on or within a substrate of the print, the memory storing data protected from overwriting relating to the print or its production and separately storing data which may be updated, the print including a transponder coupled to the memory and supported on or within the substrate, the transponder including an antenna supported on or within the substrate;

operating the transponder to receive through the air a first electromagnetic field and, in response to the first electromagnetic field received thereby, generating a second electromagnetic field, the second electromagnetic field being characteristic of the data stored in the protected memory;

operating a transceiver spaced apart from the print to transmit the first electromagnetic field through the air and for sensing the second electromagnetic field, the first electromagnetic field providing the sole source of power for the transponder; and communicating information representing data stored in the memory to a logic processor coupled to the transceiver for interpreting the information in the memory.

29. A method of assembling a storage apparatus for storing data on an output print produced by an image processing apparatus, comprising the steps of:

(a) coupling a memory to the output print, the memory adapted to store computer-readable data associated with an image;

(b) integrally coupling a transponder to the memory, the transponder adapted to receive a first electromagnetic field and, in response to the first electromagnetic field received thereby, generating a second electromagnetic field, the second electromagnetic field being characteristic of the data stored in the memory;

(c) providing a transceiver spaced-apart from the output print for transmitting the first electromagnetic field and for sensing the second electromagnetic field; and (d) coupling a logic processor to the transceiver, the logic processor adapted to communicate with the transceiver for facilitating exchange of data between the transceiver and the memory.

30. The method of claim 29, wherein the step of providing a transceiver comprises the step of providing a transceiver that transmits the first electromagnetic field at a predetermined first frequency.

31. The method of claim 29, wherein the step of providing a transceiver comprises the step of providing a transceiver that receives the second electromagnetic field at a predetermined second frequency.

32. The method of claim 29, wherein the step of coupling a memory comprises the step of coupling a memory adapted to store image processing data associated with the image.

33. The method of claim 29, wherein the step of coupling a logic processor comprises the step of coupling a logic processor that is a computer.

34. The method of claim 29, further comprising the steps of:

(a) coupling a plurality of the memories to respective ones of a plurality of the output prints; and (b) coupling a plurality of the transponders to respective ones of the memories.

35. A method of providing a print, comprising the steps of:

(a) providing a substrate;

(b) coupling a memory to the substrate, the memory adapted to store data therein;

(c) connecting a transponder to the substrate and integrally coupling the transponder to the memory, the transponder adapted to receive a first electromagnetic field and, in response to the first electromagnetic field received thereby, generate a second electromagnetic field, the second electromagnetic field being characteristic of the data stored in the memory.

36. The print of claim 35, wherein the step of providing a substrate comprises the step of providing substrate having an antenna coupled to the transponder.

37. The print of claim 35, wherein the step of coupling a memory comprises the step of coupling a memory having image processing data stored therein.

38. The print of claim 35, wherein the step of coupling a memory comprises the step of coupling a memory that is a read/write memory.

39. The print of claim 35, wherein the step of providing a substrate comprises the step of providing a paper substrate.

40. The print of claim 35, wherein the step of providing a substrate comprises the step of providing a film substrate.

* * * * *